United States Patent
Abe (10) Patent No.: US 8,197,410 B2
(45) Date of Patent: Jun. 12, 2012

(54) ULTRASONIC DIAGNOSTIC APPARATUS, ULTRASONIC IMAGE PROCESSING APPARATUS AND ULTRASONIC IMAGE PROCESSING METHOD

(75) Inventor: Yasuhiko Abe, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 690 days.

(21) Appl. No.: 12/204,369

(22) Filed: Sep. 4, 2008

(65) Prior Publication Data

US 2009/0069680 A1 Mar. 12, 2009

(30) Foreign Application Priority Data

Sep. 7, 2007 (JP) ................. 2007-233277

(51) Int. Cl.
*A61B 8/00* (2006.01)
*A61B 8/02* (2006.01)
*A61B 8/04* (2006.01)

(52) U.S. Cl. ........ 600/442; 600/437; 600/438; 600/443; 600/450; 600/463

(58) Field of Classification Search .................. None
See application file for complete search history.

(56) References Cited

U.S. PATENT DOCUMENTS

| 6,638,221 B2* | 10/2003 | Abe et al. ............... 600/437 |
| 2003/0083578 A1* | 5/2003 | Abe et al. ............... 600/447 |
| 2005/0085729 A1* | 4/2005 | Abe ............... 600/450 |

FOREIGN PATENT DOCUMENTS

| JP | 2003-175041 | 6/2003 |
| JP | 2007-117611 | 5/2007 |

OTHER PUBLICATIONS

U.S. Appl. No. 12/695,397, filed Jan. 28, 2010, Abe, et al.
Keitaro Ogawa MD, et al. "Usefulness of Automated Quantitation of Regional Left Ventricular Wall Motion by a Novel Method of Two-Dimensional Echocardiographic Tracking", 98, 2006, pp. 1531-1538.
U.S. Appl. No. 12/487,399, filed Jun. 18, 2009, Abe, et al.

\* cited by examiner

*Primary Examiner* — Unsu Jung
(74) *Attorney, Agent, or Firm* — Oblon, Spivak, McClelland, Maier & Neustadt, L.L.P.

(57) ABSTRACT

An ultrasonic diagnosis device having a data collector that collects ultrasonic image data, obtained by scanning a predetermined site of a sample periodically moving, a strain gauge setting unit that sets a predetermined number of strain gauges which includes a plurality of segments connecting two end points one or more middle points existing between the end points in the interesting area, a motion vector information generator that generates motion vector information of the tissue including at least the strain gauges, an image generator that sets a predetermined number of strain gauges in the ultrasonic image data at different time phases during the period and generates a strain gauge image in which the strain gauges are overlapped at a corresponding position, by the use of a tracking process using the set strain gauges and the motion vector information of the tissue, and a display that displays the strain gauge image.

23 Claims, 5 Drawing Sheets

ULTRASONIC DIAGNOSTIC APPARATUS, ULTRASONIC IMAGE PROCESSING APPARATUS AND ULTRASONIC IMAGE PROCESSING METHOD

CROSS-REFERENCE TO RELATED APPLICATIONS

This application is based upon and claims the benefit of priority from prior Japanese Patent Application No. 2007-233277, filed Sep. 7, 2007, the entire contents of which are incorporated herein by reference.

BACKGROUND OF THE INVENTION

The present invention relates to an ultrasonic diagnosis device, an ultrasonic image processing device, and an ultrasonic image processing method for supporting intuitive grasp of a complex wall motion due to a multi-layered structure of a cardiac muscle, for example, by overlapping and displaying gauges divided between inner and outer membranes of a heart with an ultrasonic image when strain is observed using the ultrasonic image.

It is very important in diagnosing a biological tissue such as a cardiac muscle to objectively and quantitatively estimate functions of the biological tissue. In recent years, a variety of quantitative estimation methods were tried mainly for the heart.

For example, a technique called speckle tracking of calculating local wall motion information such as displacement and strain while locally matching patterns in an image has been put into practice (for example, Patent Document 1). For example, as described in Japanese Unexamined Patent Application Publication No. 2003-175041, Japanese Unexamined Patent Application Publication No. 2007-117611, and the paper of Osaka City University, written by Ogawa et al., Am J Cardiol 2006; 98: 1531-1538, a strain gauge display method of displaying a "strain gauge" connecting a pair of two points for measurement of strain using the speckle tracking was suggested.

However, in the past display of strain gauge, only the movement state of a segment between two points connecting an inner membrane position and an outer membrane position is expressed and thus the motion information of the cardiac tissue obtained therefrom is limited. Accordingly, it was not possible to observe the detailed wall motion in which the cardiac muscle having a multi-layered structure is divided into the inner membrane side and the outer membrane side.

BRIEF SUMMARY OF THE INVENTION

The invention is contrived in view of the above-mentioned situation. An object of the invention is to provide an ultrasonic diagnosis device, an ultrasonic image processing device, and an ultrasonic image processing method for supporting the intuitive grasp of a complex cardiac motion due to the multi-layered structure of the cardiac muscle.

According to an aspect of the invention, there is provided an ultrasonic diagnosis device including: a data collecting unit configured to collect ultrasonic image data, which are obtained by scanning a predetermined site of a sample periodically moving with ultrasonic waves, during a period of one or more cycle of the motion; an interesting area setting unit configured to set a two-dimensional interesting area of a tissue in the ultrasonic image data at a predetermined time phase; a strain gauge setting unit configured to set a predetermined number of strain gauges which includes a plurality of segments connecting two end points one or more middle points existing between the end points in the interesting area; a motion vector information generating unit configured to generate motion vector information of the tissue including at least the strain gauges by the use of a process with pattern matching; an image generating unit configured to set a predetermined number of strain gauges in the ultrasonic image data at different time phases during the period and generate a strain gauge image in which the strain gauges are overlapped at a corresponding position, by the use of a tracking process using the set strain gauges and the motion vector information of the tissue; and a display unit configured to display the strain gauge image in a predetermined form.

According to another aspect of the invention, there is provided an ultrasonic image processing device including: a memory unit configured to store ultrasonic image data, which are collected by scanning a predetermined site of a sample periodically moving with ultrasonic waves, during a period of one or more cycle of the motion; an interesting area setting unit configured to set a two-dimensional interesting area of a tissue in the ultrasonic image data at a predetermined time phase; a strain gauge setting unit configured to set a predetermined number of strain gauges which includes a plurality of segments connecting two end points one or more middle points existing between the end points in the interesting area; a motion vector information generating unit configured to generate motion vector information of the tissue including at least the strain gauges by the use of a process with pattern matching; an image generating unit configured to set a predetermined number of strain gauges in the ultrasonic image data at different time phases during the period and generate a strain gauge image in which the strain gauges are overlapped at a corresponding position, by the use of a tracking process using the set strain gauges and the motion vector information of the tissue; and a display unit configured to display the strain gauge image in a predetermined form.

According to yet another aspect of the invention, there is provided an ultrasonic image processing method including: setting a two-dimensional interesting area of a tissue at a predetermined time phase in ultrasonic image data, which are collected by scanning a predetermined site of a sample periodically moving with ultrasonic waves, during a period of one or more cycle of the motion; setting a predetermined number of strain gauges which includes a plurality of segments connecting two end points one or more middle points existing between the end points in the interesting area; generating motion vector information of the tissue including at least the strain gauges by the use of a process with pattern matching; setting a predetermined number of strain gauges in the ultrasonic image data at different time phases during the period and generating a strain gauge image in which the strain gauges are overlapped at a corresponding position, by the use of a tracking process using the set strain gauges and the motion vector information of the tissue; and displaying the strain gauge image in a predetermined form.

DETAILED DESCRIPTION OF THE INVENTION

Hereinafter, embodiments of the invention will be described with reference to the accompanying drawings. In the following description, elements having substantially like functions and configurations will be denoted by like reference numerals or signs and the repeated description thereof is made only if necessary.

In this embodiment, the technical idea of the invention is applied to an ultrasonic diagnosis device. However, the invention is not limited to the ultrasonic diagnosis device, but the technical idea of the invention can be applied to an ultrasonic image processing device using a work station or a personal computer.

Functions embodied by the elements of this embodiment, particularly, functions embodied by a motion vector processing unit 19, a gauge setting unit 36, and a rotational difference information generating unit 37 (see FIG. 1) to be described later, can be also embodied by installing software programs for performing the same processes as the above-mentioned functions in a computer such as a work station or an ultrasonic diagnosis device having the function of the computer and developing the software programs in the memory thereof. At this time, the programs allowing the computer to perform the functions may be stored in a recording medium such as a magnetic disc (such as Floppy (registered trademark) disc, hard disc), an optical disc (such as CD-ROM and DVD), and a semiconductor memory and then distributed.

Figure 1:
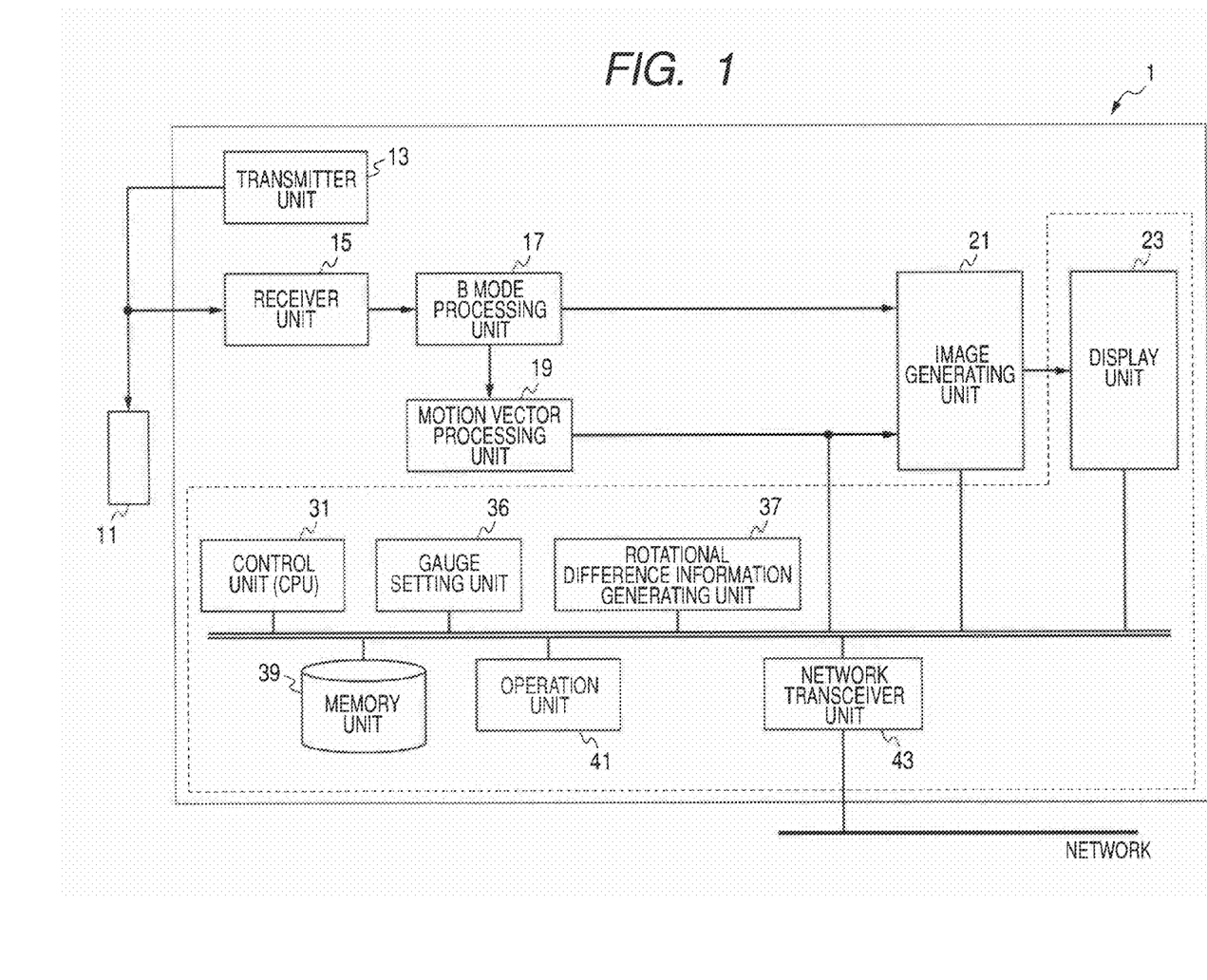
FIG. 1 is a diagram illustrating a configuration of an ultrasonic diagnosis device 1 according to an embodiment of the invention.

FIG. 1 is a diagram illustrating a configuration of an ultrasonic diagnosis device 1 according to an embodiment of the invention. The ultrasonic diagnosis device 1 includes an ultrasonic probe 11, a transmitter unit 13, a receiver unit 15, a B mode processing unit 17, a motion vector processing unit 19, an image generating unit 21, a display unit 23, a control unit (CPU) 31, a gauge setting unit 36, a rotational difference information generating unit 37, a memory unit 39, a manipulation unit 41, a network transceiver unit 43. When the invention is applied to an ultrasonic image processing unit, the elements within the dotted line in FIG. 1 serve as the elements thereof.

The ultrasonic probe 11 includes plural piezoelectric vibrators generating ultrasonic waves on the basis of driving signals from the transmitter unit 13 and converting reflected waves from a sample into electrical signals, an alignment layer disposed in the piezoelectric vibrators, and a backing material preventing the ultrasonic waves from propagating backward from the piezoelectric vibrators. When an ultrasonic wave is transmitted to the sample from the ultrasonic probe 11, various harmonic components are generated with the propagation of the ultrasonic wave due to the non-linearity of a biological tissue. Basic waves and harmonic components of the transmitted ultrasonic wave are scattered backward due to boundaries of acoustic impedance in a body tissue and fine scattering and are received as reflected waves (echo) by the ultrasonic probe 11.

The transmitter unit 13 includes a delay circuit and a pulser circuit not shown. The pulser circuit repeatedly generates rated pulses for forming the transmitted ultrasonic wave at a predetermined rated frequency fr Hz (period: 1/fr). The delay circuit gives the rated pulses a delay time necessary to concentrate the ultrasonic waves in a beam shape every channel and determine the transmission directivity. The transmission unit 13 applies a driving pulse to each vibrator so as to form ultrasonic beams toward predetermined scan lines at times based on the rated pulses.

The receiver unit 15 includes an amplification circuit, an A/D converter, and an adder not shown. The amplification circuit amplifies the echo signals received through the probe 11 every channel. The A/D converter gives the delay time necessary to determine the reception directivity of the amplified echo signals and then the adder performs an adding process. The ultrasonic echo signals corresponding to the predetermined scan lines are generated by the adding process.

The B mode processing unit 17 generates a B mode signal corresponding to the amplitude of the ultrasonic echo by performing an envelope detecting process on the ultrasonic echo signals received from the receiver unit 15.

The motion vector processing unit 19 detects the moved positions of a tissue using a pattern matching process between two two-dimensional image data having different time phases or two volume data having different time phases and calculates motion vectors (or speeds) of the tissues on the basis of the moved position. Specifically, by acquiring an interesting area in one two-dimensional image data most similar to an interesting area in the other two-dimensional image data and calculating a distance between the interesting areas, the motion vector of a tissue can be calculated. By removing the magnitude of the motion vector (that is, the moved distance) from the temporal difference between frames of the two-dimensional image data, the moving speed of the tissue can be calculated. By performing such processes at positions in the two-dimensional image data frame by frame, spatiotemporal distribution data (motion vector information) on the tissue displacement (motion vector) or the tissue speed can be acquired.

The image generating unit 21 generates a B-mode ultrasonic image indicating a two-dimensional distribution associated with a predetermined sectional layer of the B mode signal. The image generating unit 21 generates an image (strain gauge image) having strain gauges overlapped at a corresponding position in the ultrasonic images, on the basis of the strain gauges in the respective image data set by the gauge setting unit 36. In addition, the image generating unit 21 generates an ultrasonic image in which the rotational difference information is coded in color at the corresponding position, by the use of the rotational difference information generated by the rotational difference information generating unit 37.

The display unit 23 displays the ultrasonic images, the strain gauge image, and the rotational difference information in a predetermined format on the basis of video signals from the image generating unit 21 as described later. The display unit 23 also displays markers indicating anatomic positions in the images or color bars indicating the magnitudes of color-coded physical quantities.

The control unit (CPU) 31 has a function of an information processing device (computer) and statically or dynamically controls operations of the ultrasonic diagnosis device body. Particularly, the control unit 31 performs a motion information generating function to be described later by developing exclusive programs stored in the memory unit 39 in a memory not shown.

The gauge setting unit 36 performs processes such as setting strain gauges to be described later by the use of the motion vector information output from the motion vector processing unit 19.

The rotational information generating unit 37 performs a rotational difference information generating process described later by the use of the motion vector information.

The memory unit 39 includes a recording medium such as a magnetic disc (such as Floppy (registered trademark) disc, hard disc), an optical disc (such as CD-ROM and DVD), and a semiconductor memory and a device reading out information recorded therein. The memory unit 37 stores transmission and reception conditions, predetermined scanning sequences, biological data or ultrasonic image data (for example, tissue image data photographed in a tissue Doppler mode or a B mode) corresponding to time phases, volume data for each time phase generated in advance, spatiotemporal distribution data on tissue motion vector or tissue speed, a program for embodying a motion information generating function to be described later, diagnosis information (patient ID, doctor's opinion, and the like), diagnosis protocols, body mark generating programs, and the like.

The manipulation unit 41 is connected to the device body and includes a mouse or track ball, a mode changing switch, and a keyboard for inputting various instructions from an operator, inputting instructions for setting the interesting areas (ROI), inputting various instructions for setting image quality, and selecting tissue motion information.

The network transceiver unit 43 is a device configured to transmit and received information to and from another device through a network. Data or analysis results of ultrasonic images acquired by the ultrasonic diagnosis device 1 can be transmitted to another device through the network by the network transceiver unit 43.

Motion Information Generating Function

A motion information generating function of the ultrasonic diagnosis device 1 will be described now. This function is to generate segments (gauges) for visualizing local strain of the cardiac muscle and to overlap and display the segments at the corresponding positions in the ultrasonic images. In some cases, the function is to calculate information on the rotational difference between an inner membrane and an outer membrane or information on the rotational difference between the inner membrane and the outer membrane about an intermediate membrane (a layer corresponding to the middle between the inner membrane and the outer membrane) and to display the information in a predetermined format.

In this embodiment, for the purpose of concrete explanation, the motion information generating function using the heart as a diagnosis target is exemplified. However, the target of the motion information generating function is not limited to the heart, but may be any site as long as it periodically moves.

Figure 2:
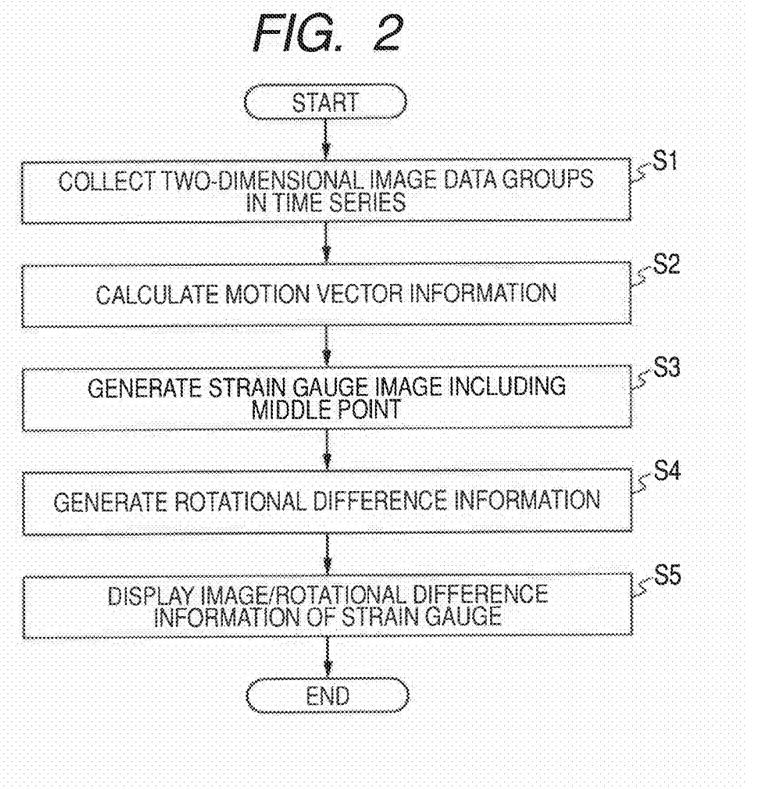
FIG. 2 is a flowchart illustrating a flow of processes (local strain gauge generating and displaying processes) corresponding to local strain gauge generating and displaying functions.

FIG. 2 is a flowchart illustrating a flow of processes (motion information generating process of the heart) corresponding to the motion information generating function. This function is described now with reference the drawing.

Step S1: Collect Data

First, time-series two-dimensional image data (hereinafter, referred to as time-series two-dimensional image data groups) of a desired observation site of a patient's heart during a period corresponding to at least one heartbeat using a predetermined time as a reference (step S1).

Step S2: Calculate Motion Vector Information

Then, tissue motion information is generated (step S2). That is, the motion vector processing unit 19 extracts an interesting area in a cardiac site from the two-dimensional image data at a predetermined time phase among the two-dimensional image data corresponding to the time phases of one or more heartbeat of the collected time-series two-dimensional image data group, on the basis of a user's instruction, and calculates spatiotemporal motion vector information by temporally tracking the extracted interesting area by the use of a two-dimensional pattern matching process. By removing the motion vector from the temporal difference between frames of the two-dimensional image data, the moving speed of the tissue can be calculated.

Step S3: Generate Strain Gauge Image Including Middle Point

Then, a process of generating a strain gauge image including a middle point is performed (step S3).

Figure 3:
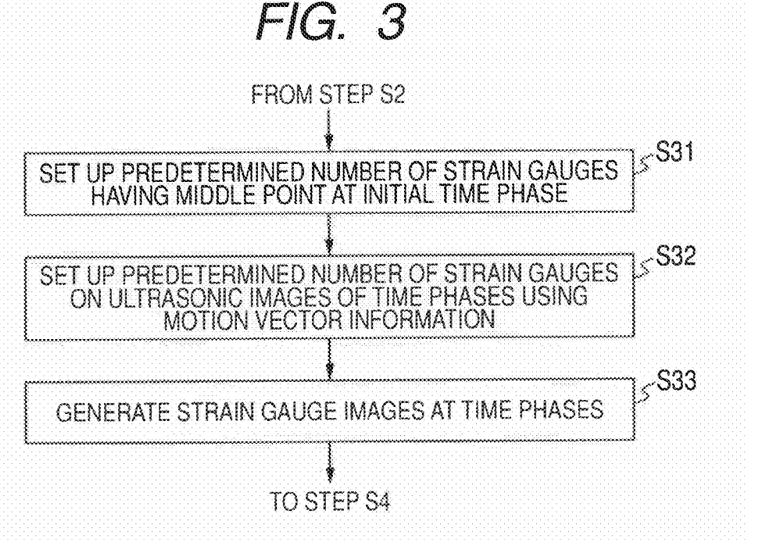
FIG. 3 is a flowchart illustrating a flow of a process performed in generating a strain gauge image.

FIG. 3 is a flowchart illustrating a flow of processes performed in generating a strain gauge image. As shown in the drawing, first, the gauge setting unit 36 sets a predetermined number of (for example, several tens) strain gauges in an ultrasonic image corresponding to a reference time phase (for example, an end-systolic time phase as an initial time phase) (step S31). That is, the gauge setting unit 36 sets an initial outline at the inner and outer membranes positions at the end-systolic time phase and sets one of the predetermined number of gauge end points in the initial outline with a constant interval (or with a constant angle about the center of endocardium). The gauge setting unit 36 sets the other of the gauge end points at positions where normal lines of the endocardoal surface in one of the respective gauge end points in the initial outline intersect the outer membrane, and connects the gauge end points to each other with segments (strain gauges) along the normal lines. The gauge setting unit 36 sets plural strain gauges including a gauge middle point by setting the gauge middle point (middle point existing in the segments connecting the gauge end points) at middle points of the strain gauges.

In this embodiment, for the purpose of concrete explanation, in order to observe movements of the inner membrane, the intermediate membrane, and the outer membrane of the cardiac muscle, one of the respective gauge end points is set in the inner membrane, the other of the respective gauge end points is set in the outer membrane, and the gauge middle point is set as a middle point between the gauge end points. However, the invention is not limited to this setting, but the positions of the gauge end points and the gauge middle points are not limited as long as they are effective for visually displaying the local strain of the cardiac muscle. In this embodiment, in order to observe the motions of the inner membrane, the intermediate membrane, and the outer membrane of the cardiac muscle, one gauge middle point is set at the middle point between a pair of gauge end points. However, the invention is not limited to the setting, but a desired number of gauge middle points may be set at desired positions as long as they are located between the gauge end points. By setting at least one middle point in this way, it is possible to define the strain gauges including plural segments.

The gauge setting unit 36 then sets the strain gauges in the ultrasonic images at different time phases by the use of the strain gauges set at the reference time phase and the motion vector information (step S32). That is, the gauge setting unit 36 sets the strain gauges at the time phases by tracking the gauge end points and the gauge middle points of the strain gauges set at the reference time phase by the use of the motion vector information.

Then, the image generating unit 21 generates a strain gauge image of each time phase in which the strain gauges are overlapped at positions corresponding to the ultrasonic image (step S33).

Step S4: Generate Rotational Difference Information

Figure 4:
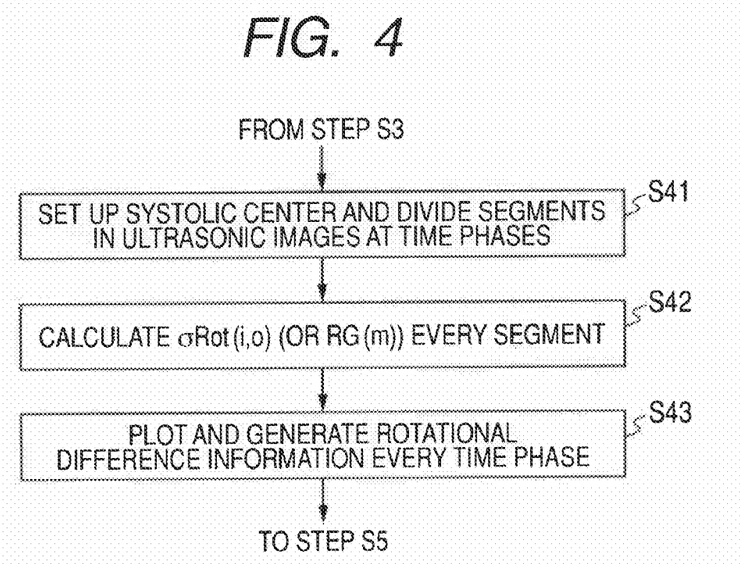
FIG. 4 is a flowchart illustrating a flow of processes performed in generating rotational difference information.

The rotational difference information generating unit 37 generates the rotational difference information (step S4).

FIG. 4 is a flowchart illustrating a flow of processes performed in generating the rotational difference information. First, the rotational difference generating unit 37 sets a systolic center in the ultrasonic image at the respective time phases and calculates the rotational difference information for each anatomic segment of the cardiac site (step S41). The setting of the systolic center employs, for example, the center position of the inner membrane. The assignment of anatomic segment (segmentation) can be carried out by assigning a predetermined section as a display format at the time of collecting data and allowing a user to adjust the position of the probe in accordance with the display format. By the segmentation, the cardiac muscle is partitioned into anatomic areas such as Sep/Ant/Lat/Post/Inf.

The rotational difference information generating unit 37 calculates the rotational information on the areas of the cardiac muscle at the time phases by the use of Expression 1 (step S42), in the unit of degree in which a direction where the positions of the inner and outer membranes rotates counterclockwise about the center position of the inner membrane at an end-diastolic time phase is positive and the clockwise direction is negative.

$$\delta Rot(i,o) = Rot(i) - Rot(o) \quad \text{Expression 1}$$

Here, $\delta Rot(i,o)$ represents a rotational difference value of the outer membrane relative to the inner membrane, $Rot(i)$ represents a rotation angle of the inner membrane in the respective areas, and $Rot(o)$ represents a rotation angle of the outer membrane in the respective areas.

Figure 5:
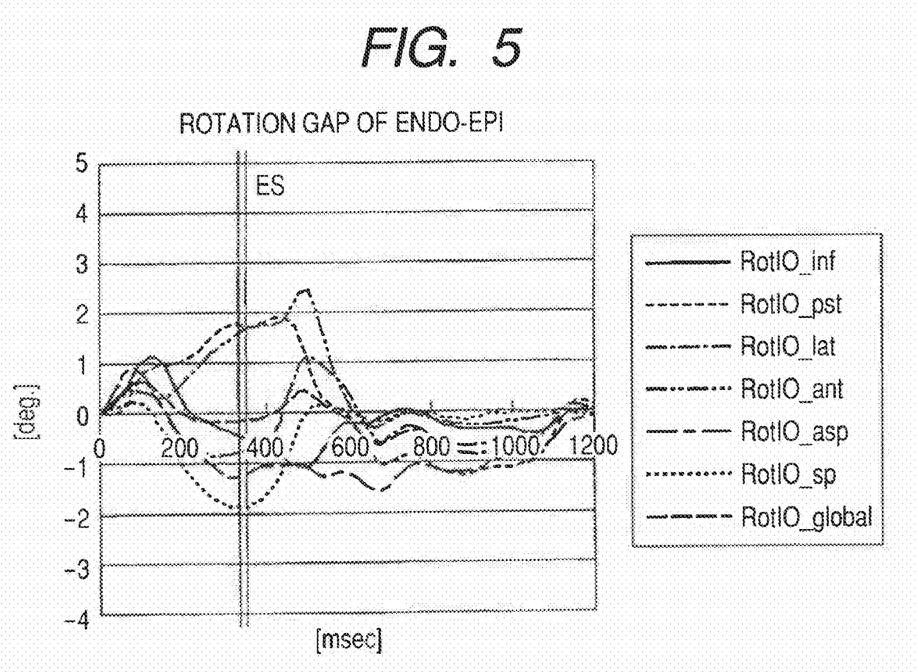
FIG. 5 is a diagram illustrating an example of inner-outer rotational difference information.

The rotational difference information generating unit 37 generates the rotational difference information shown in FIG. 5 by plotting the rotational information of the areas of the cardiac muscle every time phase (step S43). In FIG. 5, "ES" represents the end-systolic time phase and "global" represents an average of the global cardiac muscle.

In the above-mentioned example, Expression 1 for calculating the rotational difference information from the information of only the inner membrane and the outer membrane is used. However, the invention is not limited to it, but for example, the rotational difference information may be calculated using Expression 2 in which the motion of the intermediate membrane is considered.

That is, the rotational information RG(m) which is the rotational difference between the intermediate membrane and the outer membrane relative to the rotational difference between the inner membrane and the intermediate membrane is calculated on the areas of the cardiac muscle at the time phases by the use of Expression 2 (step S42), in the unit of degree in which a direction where the positions of the inner and outer membranes and the intermediate membranes rotate counterclockwise about the center position of the inner membrane at the end-diastolic time phase is positive and the clockwise direction is negative.

$$\begin{aligned} RG(m) &= \delta Rot(i, m) - \delta Rot(m, o) \quad \text{Expression 2} \\ &= Rot(i) - Rot(m) - (Rot(m) - Rot(o)) \\ &= Rot(i) - 2^* Rot(m) + Rot(o) \end{aligned}$$

Here, $Rot(i)$ represents the rotation angle of the inner membrane of the respective areas, $Rot(o)$ represents the rotation angle of the outer membrane in the respective areas, and $Rot(m)$ is the rotational angle of the intermediate membrane in the respective areas.

Figure 6:
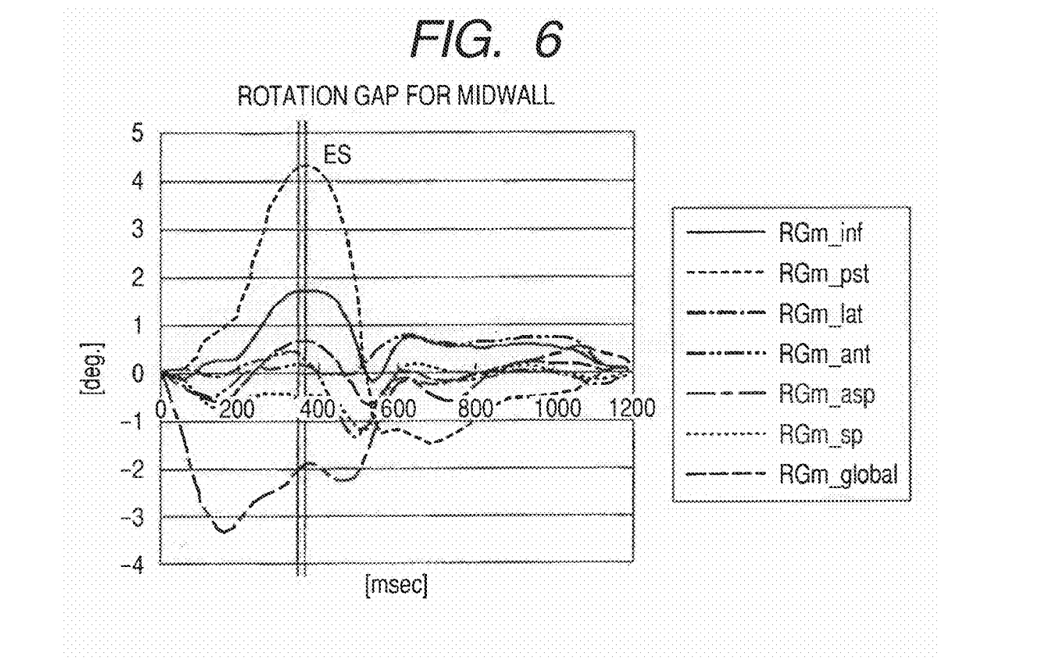
FIG. 6 is a diagram illustrating another example of the inner-outer rotational difference information.

In this case, the rotational difference information generating unit 37 generates the inner and outer rotational difference information shown in FIG. 6, by plotting the rotational information of the respective areas of the cardiac muscle every time phase (step S43). In FIG. 6, similarly, "ES" represents the end-systolic time phase and "global" represents the average value of the global cardiac muscle.

Step S5: Display Rotational Difference Information of Strain Gauge Image

The display unit 23 then displays the strain gauge image in a predetermined format (step S5).

Figure 7:
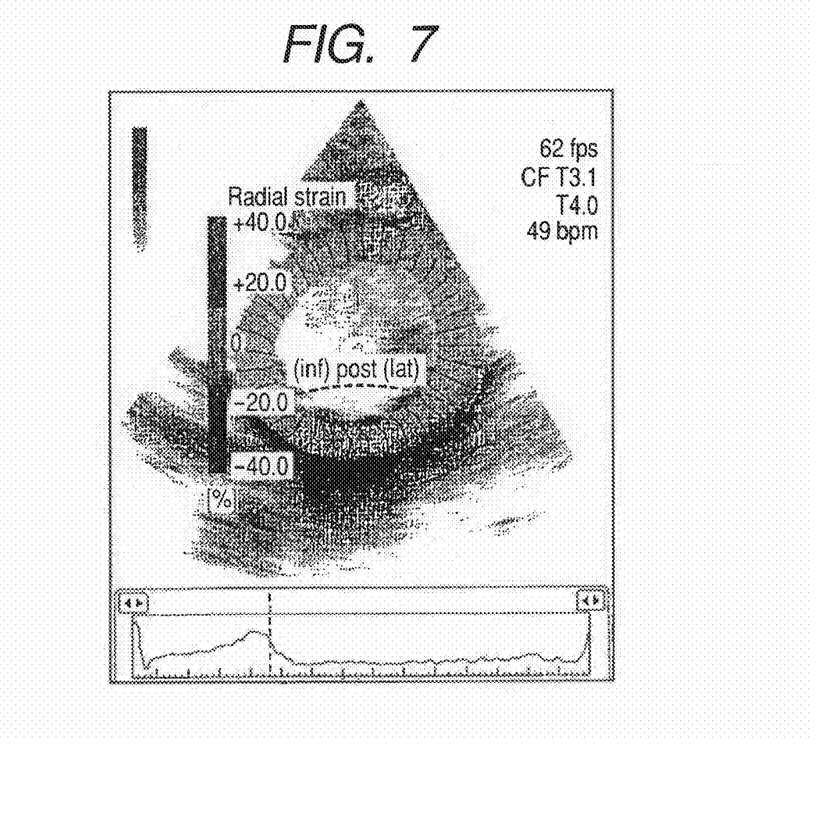
FIG. 7 is a diagram illustrating an example of a display format of the strain gauge image using a gauge middle point.

FIG. 7 is a diagram illustrating an example (where image data of a normal person is used to correspond to the end-diastolic time phase in which the strain tracking is started at the end-systolic time phase) of a display format of the strain gauge image. As can be seen from the drawing, the tracking result of the inner and outer membrane positions and the intermediate membrane positions up to the end-diastolic time phase by the use of the strain gauges including the middle points set in the intermediate membrane area in the speckle tracking method is obtained. Supporting information (that is, character information of Sept/Ant/Lat/Post/Inf) for orientating the anatomic segments of the cardiac site of the respective images are assigned to the corresponding cardiac wall positions and displayed by markers. In addition, the correspondence of the images for orientation and the anatomic segments can be carried out by assigning a predetermined section (such as parasternal short-axis riew) as a display format at the time of collecting data and allowing a user to adjust the position of the probe in accordance with the display format.

Figure 8:
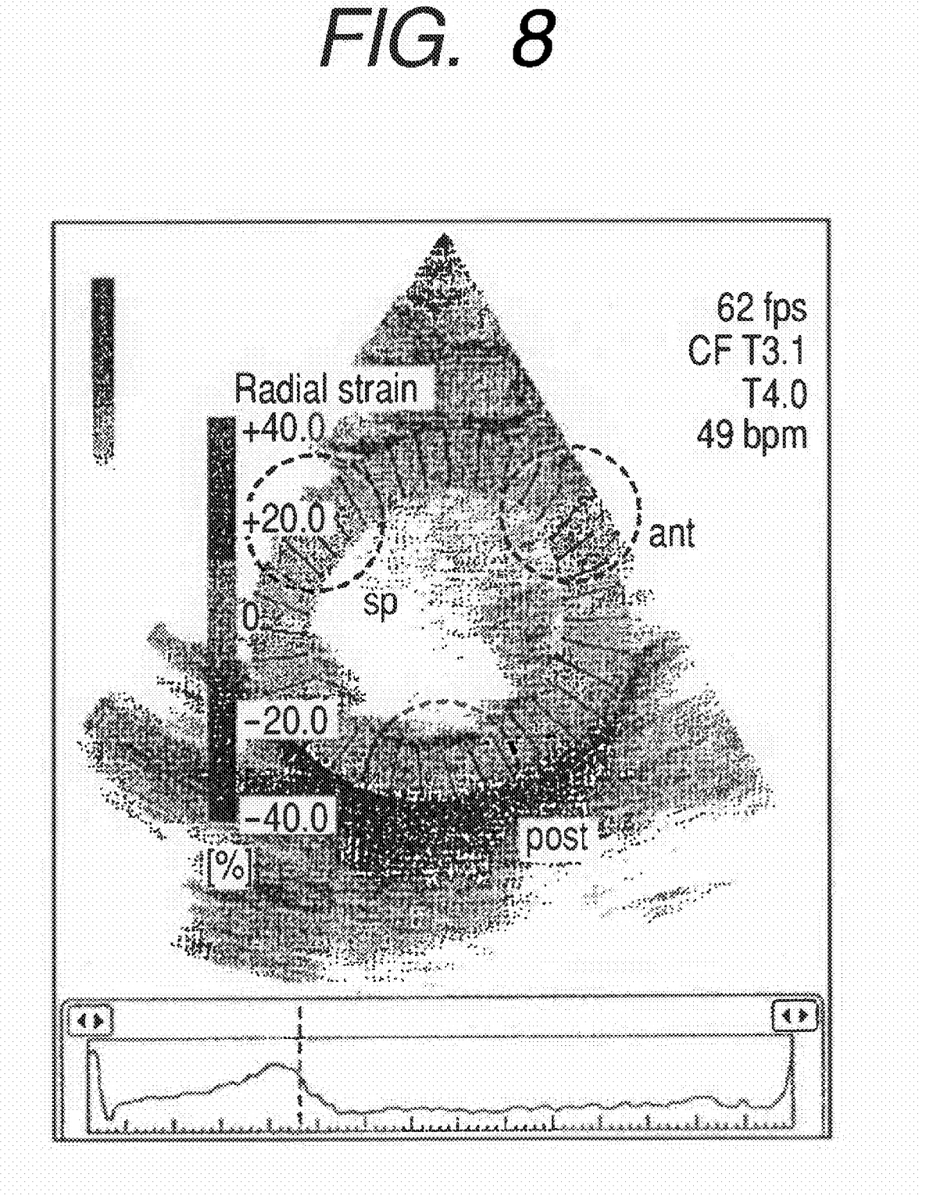
FIG. 8 is a diagram illustrating an example of a strain gauge image using a strain gauge not having a gauge middle point.

In the strain gauge image shown in FIG. 7, for example, paying attention to the posterior wall (pst) site, in the example shown in FIG. 8 (that is, a gauge strain including the end points in the inner membrane not having the gauge middle point and the end point in the outer membrane is used), the rotational difference between the inner and outer membranes is shown, but the degree of rotation of the intermediate membrane position is smaller than those of the inner and outer membranes. In addition, the strain gauge strained in the shape of "<" can be observed. This means that the complex wall motion due to the multi-layered structure of the cardiac muscle can be intuitively grasped by the use of the strain gauges having the middle point and the strain gauge image in which the strain gauges are overlapped.

More specifically, to correspond to the three-layer structure of the cardiac muscle including an oblique layer, a circular layer, and a longitudinal layer, it can be considered that the inner membrane, the intermediate membrane, and the outer membrane of the layers express complex motions with the systole and diastole motions of the heart. This phenomenon cannot be grasped by the past method and is information first provided by the strain gauges having the middle point and the strain gauge image having the strain gauges. In this embodiment, the heart is understood as a three-layer structure to visualize the systolic and diastolic motions thereof. However, it is only an example that the heart is understood as the three-layer structure. For example, when the heart is understood as a four-layer structure or more, the systolic and diastolic motions of the layers can be visualized by setting plural gauge middle points or gauge end points to correspond to the layers (for example, setting them at the center positions or boundaries of the layers).

In FIG. 7, a normal person is exemplified. On the contrary, in case of a patient having an ischemic cardiac disease, it is known that the subendocardial side of the heart is first disordered. Accordingly, when the local myocardial ischemia is derived by load echo, it is clinically useful that the strain gauges having the middle points before and after the load and the strain gauge images including the strain gauges are observed and compared. When the inner membrane side is disordered after the stress to cause the variation in motion before the stress, it is expected that this state can be intuitively understood as a variation in which the "<" shape of the strain gauge display according to the invention is bent by the image diagnosis, compared with the past observation. The same advantages can be expected for the observation of the variation of the wall motion before and after treatment using medicine or the like, not before and after the stress. The comparison and observation of the time-series ultrasonic image data or the ultrasonic image data collected with a time gap such as before and after treatment or before and after stress using the motion information generating function can be said to be a suitable application of the ultrasonic diagnosis device 1 according to this embodiment.

In this embodiment, by using the end-systolic time phase as an initial time phase and setting an initial outline in the ultrasonic image data at the corresponding time phase, the variation resulting from the tracking up to the end-diastolic time phase is visualized by the use of the strain gauge image. However, for example, by using the end-diastolic time phase as an initial time phase and setting an initial outline in the ultrasonic image data at the corresponding time phase, the variation resulting from the tracking up to the end-systolic time phase may be visualized by the use of the strain gauge image.

In addition, according to the speckle tracking method, since the intermediate membrane can be tracked in principle also in a apical view, the observation can be carried out by the use of the motion information generating function using the apical view as well as a short axis view shown in this embodiment. In the apical view, the distance in moved distance between the layers of the inner and outer membranes with the shortening motion in the long axis direction can be intuitively displayed by the use of the strain gauge, rather than the rotational components of the inner and outer membranes and for example, it can be easily seen which of the inner membrane side and the outer membrane side contributes to the increase in wall thickness.

The rotational difference information (see FIGS. 5 and 6) generated in step S4 is displayed in a predetermined format. By displaying the rotational difference information in this way, the rotational difference of the inner and outer membranes in the respective areas of the cardiac muscle or the global cardiac muscle or the rotational difference of the inner membrane side and the outer membrane side relative to the intermediate membrane can be quantitatively expressed, thereby analyzing the temporal variation thereof as shown in the graph.

By converting the acquired rotational difference parameter into color codes and overlapping and displaying them in the B mode to correspond to each other in position, the parametric-imaging providing new wall motion information is also possible.

In order to grasp the temporal variation of the rotational difference information on the ultrasonic image data acquired at different time phases, the information on the temporal variation of the rotational difference information may be generated using a process including the difference of the rotational difference information may be then displayed in a predetermined format. In this way, by displaying the variation result, which is acquired by the process including the difference of the inner and outer rotation, in graph or in parametric-imaging, it is possible to support the grasp of the degree of temporal variation in wall motion as a suitable application of the ultrasonic diagnosis device.

Advantages

According to the above-mentioned configuration, the following advantages can be obtained.

In the ultrasonic diagnosis device, plural strain gauges which are bent segments defined by the gauge end points and the gauge middle points are set at the respective time phases using the motion vector information of tissue and the strain gauge image is generated and displayed in which the strain gauges are overlapped at the corresponding positions of the ultrasonic image at the time phases. An observer can individually observe the motions of the inner membrane, the intermediate membrane, and the outer membrane by the use of the displayed strain gauge image. As a result, it is possible to support the intuitive grasp of the complex wall motion due to the multi-layered structure of the cardiac muscle.

In the ultrasonic diagnostic device, the rotation angles from the reference time phase are calculated and the rotational difference information between the gauge end points (and the gauge middle points if necessary) is generated and displayed in a predetermined format. Accordingly, for example, by setting the gauge end points in the inner membrane and the outer membrane of the cardiac muscle and setting the gauge middle points in the intermediate membrane, the quantitative information such as the rotational difference of the inner and outer membranes in the respective areas of the cardiac muscle or the global cardiac muscle or the rotational difference of the inner membrane side and the outer membrane side relative to the intermediate membrane is generated. In addition, the temporal variation can be analyzed by the use of graph. As a result, it is possible to support the intuitive grasp of the complex wall motion due to the multi-layered structure of the cardiac muscle.

The invention is not limited to the embodiment, but the elements thereof may be modified in various forms at the stage of practice without departing from the gist of the invention. Specific modified examples include the followings.

In the above-mentioned embodiment, it is described that the strain gauge image or the rotational difference information is generated and displayed using the strain gauges having the gauge middle point. On the contrary, in the ultrasonic diagnosis device, the strain gauge image or the rotational difference information may be generated and displayed using the strain gauges (that is, strain gauges including one end point in the inner membrane and the other end point in the outer membrane) not having the gauge middle point. This can be embodied by omitting the process of setting of the middle point in step S3 or the like.

FIG. 8 is a diagram illustrating an example (where image data of a normal person is used to correspond to the end-diastolic time phase in which the strain tracking is started at the end-systolic time phase) of the strain gauge image using the strain gauges not having the gauge middle point. In the drawing, paying attention to the individual sites of the front wall (ant), the intermediate wall (sp), and the back wall (pst), it can be seen that the directions of the segments are not perpendicular to the inner membrane surface. That is, in the sites, it means that a difference exists between the degree of rotation of the inner membrane (about the center) and the degree of rotation of the outer membrane generated from the end-systolic time phase to the end-diastolic time phase. On the other hand, in the other sites, it can be considered that the degree of rotation of the inner membrane and the degree of rotation of the outer membrane generated from the end-systolic time phase to the end-diastolic time phase are substantially equivalent to each other with the directions of segments perpendicular to the inner membrane surface. It is possible to intuitively grasp the difference in degree of rotation as well as the variation in distance (variation in wall thickness) between the inner and outer membranes, by the use of the strain gauge image using the strain gauges not having the gauge middle point. The display format of the rotational difference information is as described above.

The invention can be modified in various forms by properly combining the elements described in the above-mentioned embodiment. For example, some elements may be deleted from the entire elements described in the above-mentioned embodiment. The elements of the different embodiments may be properly combined.

What is claimed is:

1. An ultrasonic diagnosis device comprising:
a data collecting unit configured to collect ultrasonic image data, which are obtained by scanning a predetermined site of a sample periodically moving with ultrasonic waves, during a period of one or more cycle of the motion;
an interesting area setting unit configured to set a two-dimensional interesting area of a tissue of the sample in the ultrasonic image data at a predetermined time phase;
a strain gauge setting unit configured to set a predetermined number of strain gauges which includes a plurality of segments connecting two end points to one or more middle points existing between the end points in the interesting area;
a motion vector information generating unit configured to generate motion vector information of the tissue including at least the strain gauges by the use of a process with pattern matching;
an image generating unit configured to set a predetermined number of strain gauges in the ultrasonic image data at different time phases during the period and generate a strain gauge image in which the strain gauges are overlapped at a corresponding position, by the use of a tracking process using the set strain gauges and the motion vector information of the tissue; and
a display unit configured to display the strain gauge image in a predetermined form.

2. The ultrasonic diagnosis device according to claim 1, wherein the predetermined site of the sample is a heart,
wherein one of the end points is set at a position relative to an inner myocardial membrane and another one of the end points is set at a position relative to an outer myocardial membrane, and
wherein the strain gauges are set in the transmural direction of the heart of the sample.

3. The ultrasonic diagnosis device according to claim 2, wherein the middle point is set at a position inside the myocardium of the heart.

4. The ultrasonic diagnosis device according to claim 2, wherein the setting unit sets a center of rotation in the ultrasonic image data at the plurality of time phases including a reference time phase,
wherein the ultrasonic diagnosis device further includes:
a calculation unit configured to calculate rotation angles of a first end point, a second end point, and the middle point about the center of rotation for each of the strain gauges in the ultrasonic image data at the time phases; and
a rotational difference information generating unit configured to generate a rotational difference indicating a difference between a rotation angle of the inner myocardial membrane side and a rotation angle of the outer myocardial membrane side using the rotation angles of the first end point, the second end point, and the middle point at the reference time phase, and
wherein the display unit displays the rotational difference information in a predetermined format.

5. The ultrasonic diagnosis device according to claim 4, wherein the rotational difference information generating unit generates the rotational difference information every anatomic segment of the myocardial membrane of the heart.

6. The ultrasonic diagnosis device according to claim 4, wherein the image generating unit generates the strain gauge image in which the difference between the rotation angle of the inner myocardial membrane and the rotation angle of the outer myocardial membrane is coded in color based on the rotational difference information and the strain gauge image is matched with the corresponding position of the ultrasonic image data.

7. The ultrasonic diagnosis device according to claim 4, wherein the rotational difference information generating unit generates a temporal variation curve of the rotation angles as the rotational difference information.

8. The ultrasonic diagnosis device according to claim 4, wherein the rotational difference information generating unit generates information on a temporal variation of the rotational difference information by subtracting two pieces of rotational difference information generated using two different ultrasonic image data, and
wherein the display unit displays the information on the temporal variation of the rotational difference information in a predetermined format.

9. The ultrasonic diagnosis device according to claim 1, wherein the display unit concurrently or alternately displays a before-treatment strain gauge image and an after-treatment strain image or the before-stress strain gauge image and the after-stress strain gauge image.

10. The ultrasonic diagnosis device according to claim 1, wherein the predetermined site of the sample is a heart, and
wherein one of the end points is set at a position corresponding to an inner myocardial membrane, the other of the end points is set at a position corresponding to an outer myocardial membrane, and the one or more middle points are set at a position corresponding to the outer myocardial membrane.

11. The ultrasonic diagnosis device according to claim 1, wherein the predetermined site of the sample is a heart, and
wherein the two end points and the one or more middle points are set to correspond to a plurality of layers of a cardiac muscle of the heart or boundaries thereof, respectively.

12. An ultrasonic image processing device comprising:
a memory unit configured to store ultrasonic image data, which are collected by scanning a predetermined site of a sample periodically moving with ultrasonic waves, during a period of one or more cycle of the motion;
an interesting area setting unit configured to set a two-dimensional interesting area of a tissue of the sample in the ultrasonic image data at a predetermined time phase;
a strain gauge setting unit configured to set a predetermined number of strain gauges which includes a plurality of segments connecting two end points to one or more middle points existing between the end points in the interesting area;
a motion vector information generating unit configured to generate motion vector information of the tissue including at least the strain gauges by the use of a process with pattern matching;

an image generating unit configured to set the predetermined number of strain gauges in the ultrasonic image data at different time phases during the period and generate a strain gauge image in which the strain gauges are overlapped at a corresponding position, by the use of a tracking process using the set strain gauges and the motion vector information of the tissue; and a display unit configured to display the strain gauge image in a predetermined form.

13. An ultrasonic image processing method comprising:

setting a two-dimensional interesting area of a tissue at a predetermined time phase in ultrasonic image data, which are collected by scanning a predetermined site of a sample including the tissue periodically moving with ultrasonic waves, during a period of one or more cycle of the motion;

setting a predetermined number of strain gauges which includes a plurality of segments connecting two end points to one or more middle points existing between the end points in the interesting area;

generating motion vector information of the tissue including at least the strain gauges by the use of a process with pattern matching;

setting the predetermined number of strain gauges in the ultrasonic image data at different time phases during the period and generating a strain gauge image in which the strain gauges are overlapped at a corresponding position, by the use of a tracking process using the set strain gauges and the motion vector information of the tissue; and displaying the strain gauge image in a predetermined form.

14. The ultrasonic image processing method according to claim 13, wherein the predetermined site of the sample is a heart, wherein one of the end points is set at a position relative to an inner myocardial membrane and another one of the end points is set at a position relative to an outer myocardial membrane, and wherein the strain gauges are set in the transmural direction of the heart of the sample.

15. The ultrasonic image processing method according to claim 14, wherein the middle point is set at a position inside the myocardium of the heart.

16. The ultrasonic image processing method according to claim 14, further comprising:

setting a center of rotation of the heart in the ultrasonic image data at the plurality of time phases including a reference time phase;

calculating rotation angles of a first end point, a second end point, and the middle point at the reference time phase about the systolic center for each of the strain gauges in the ultrasonic image data at the time phases;

generating a rotational difference indicating a difference between a rotation angle of the inner myocardial membrane side and a rotation angle of the outer myocardial membrane side using the rotation angles of the first end point, the second end point, and the middle point at the reference time phase; and displaying the rotational difference information in a predetermined format.

17. The ultrasonic image processing method according to claim 16, wherein the generating of the rotational difference information includes generating the rotational difference information every anatomic segment of the myocardial membrane of the heart.

18. The ultrasonic image processing method according to claim 16, wherein the generating of the strain image includes generating the strain gauge image in which the difference between the rotation angle of the inner myocardial membrane and the rotation angle of the outer myocardial membrane is coded in color based on the rotational difference information and the strain gauge image is matched with the corresponding position of the ultrasonic image data.

19. The ultrasonic image processing method according to claim 16, wherein the generating of the rotational difference information includes generating a temporal variation curve of the rotation angles as the rotational difference information.

20. The ultrasonic image processing method according to claim 16, wherein information on the temporal variation of the rotational difference information is generated by subtracting two pieces of rotational difference information generated using two different ultrasonic image data, and wherein the information on the temporal variation of the rotational difference information is displayed in a predetermined format.

21. The ultrasonic image processing method according to claim 13, wherein the displaying includes concurrently or alternately displaying a before-treatment strain gauge image and an after-treatment strain image or the before-stress strain gauge image and the after-stress strain gauge image.

22. The ultrasonic image processing method according to claim 13, wherein the predetermined site of the sample is a heart, and wherein one of the end points is set at a position corresponding to an inner myocardial membrane, the other of the end points is set at a position corresponding to an outer myocardial membrane, and the one or more middle points are set at a position corresponding to the outer myocardial membrane.

23. The ultrasonic image processing method according to claim 13, wherein the predetermined site of the sample is a heart, and wherein the two end points and the one or more middle points are set to correspond to a plurality of layers of a cardiac muscle of the heart or boundaries thereof, respectively.

* * * * *